US006488640B2

(12) United States Patent
Hood, Jr. et al.

(10) Patent No.: US 6,488,640 B2
(45) Date of Patent: Dec. 3, 2002

(54) METHOD AND DEVICE FOR CONTINUOUS PASSIVE LUMBAR MOTION (CLMP) FOR BACK EXERCISE

(76) Inventors: Robert T. Hood, Jr., P.O. Box 820, Damariscotta, ME (US) 04401; David H. Little, 29 Little La., Nobleboro, ME (US) 04555

(*) Notice: Subject to any disclaimer, the term of this patent is extended or adjusted under 35 U.S.C. 154(b) by 7 days.

(21) Appl. No.: 09/435,741

(22) Filed: Nov. 8, 1999

(65) Prior Publication Data

US 2002/0058891 A1 May 16, 2002

(51) Int. Cl.$^{7}$ .................................................. A61M 1/00
(52) U.S. Cl. .............................................. 601/23; 472/95
(58) Field of Search .............................. 601/23, 24, 26, 601/89–93, 97, 98, 101; 5/101, 108, 109; 273/338; 434/247, 365; 472/97, 29, 95, 96; 280/1.201, 1.206, 1.207; 104/61

(56) References Cited

U.S. PATENT DOCUMENTS 3,480 A * 3/1844 Halsted ...................... 482/142
812,997 A * 2/1906 Himburg
1,207,023 A * 12/1916 Grellner
1,468,993 A * 9/1923 Converse
1,555,028 A * 4/1925 Roth
2,560,404 A * 7/1951 Assmar ....................... 128/33
2,566,983 A * 9/1951 Coltrane ........................ 5/109
3,019,740 A * 2/1962 Price ........................... 104/61
3,628,620 A * 12/1971 Byers ........................ 180/1 D
3,793,962 A * 2/1974 Sights ......................... 104/61
3,997,979 A * 12/1976 Turner ......................... 472/29
4,586,492 A * 5/1986 Manahan ..................... 601/90
4,830,388 A * 5/1989 Wang ......................... 280/202
4,949,712 A * 8/1990 Troii ........................ 128/25 R
4,981,131 A 1/1991 Hazard
4,986,260 A 1/1991 Iams et al.
4,986,534 A * 1/1991 Meier et al. .................. 272/96
4,988,300 A * 1/1991 Yamaguchi et al. ........ 434/247
5,050,865 A * 9/1991 Augspurger et al. ........... 482/2
5,085,425 A * 2/1992 Collins et al. ................ 472/97
5,107,822 A * 4/1992 Ohashi ...................... 128/25 R
5,123,701 A * 6/1992 Bottamiller et al. ........ 297/261
5,407,408 A * 4/1995 Wilkinson ................... 482/54
5,411,469 A * 5/1995 Wang .......................... 601/84
5,468,216 A 11/1995 Johnson et al.
5,500,002 A 3/1996 Riddle et al.
5,520,614 A * 5/1996 McNamara et al. .......... 601/24
5,572,903 A * 11/1996 Lee ............................... 5/109
5,624,383 A 4/1997 Hazard et al.
5,637,076 A 6/1997 Hazard et al.
5,816,818 A * 10/1998 Wun ........................... 434/29
5,941,800 A * 8/1999 Laconis ....................... 482/70
6,027,432 A * 2/2000 Cheng ......................... 482/57
6,056,706 A * 5/2000 Hung .......................... 601/89
6,251,123 B1 * 6/2001 Patner ........................ 606/237

OTHER PUBLICATIONS

"The Benefits of Thernapeutic Riding," http://www.instanet.com/~sert/physical.html online through at least Nov. 1, 1999.

The Power of CPM: Healing Through Motion,: by Steven L. Diehm, Continuing Care, vol. 8, No. 10, Nov. 1989.

"North American Riding for the Handicapped Association," http://www.narha.org/aha.html online through at least Nov. 1, 1999.

"Helping Your Back Pain Patients Make the Most of Spinal Motion," Rowland G. Hazard, M.D., et. al., Jr of Musculoskelatal Medicine, vol. 11, No. 1, Jan. 1994.

"Continuous Passive Motion in Seating: A New Strategy Against Low Back Pain," Steven M. Reinecke, et. al., Jr of Spinal Disorders, vol. 7, No. 1, Jan. 1994.

* cited by examiner

*Primary Examiner*—Justine R. Yu

(57) ABSTRACT

An continuous passive lumbar motion (CPLM) device for alleviating lower back stiffness and/or pain. A person seated on a backless seat is subjected to cyclical forward and backward horizontal acceleration, thus imposing a horizontal to-and-fro force to the lower part of the body resulting in flexion and tension of the upper torso relative to the lower torso in the lumbar spinal region.

13 Claims, 3 Drawing Sheets

METHOD AND DEVICE FOR CONTINUOUS PASSIVE LUMBAR MOTION (CLMP) FOR BACK EXERCISE

BACKGROUND OF THE INVENTION

1. Field of the Invention

The present invention relates generally to the field of physical exercise and, in particular, to that of exercise leading to an enhanced range of back motion and concurrent reduction in back discomfort. More particularly, the present invention relates to an exercise device and method for applying continuous passive motion (CPM) to the lumbosacral spine. More particularly yet, the present invention relates to such a device and method that causes the lower body of the person being exercised to move back and forth horizontally in a motion mimicking that experienced by a horseback rider on a horse at the walk, thereby subjecting the lumbosacral spine to repetitious flexion and extension resulting in rotating the pelvis, a movement called pelvic tilting.

2. Description of the Prior Art

Limited back motion may be a normal function of back configuration, varying greatly from individual to individual, or it may be abnormal reflecting some structural change resulting from genetic deformity or some degenerative or traumatic process causing arthritic deformation, either recognized or unrecognized. Nevertheless, most limitations of back motion and, hence, most incidences of back pain, are not associated with an identifiable anatomic deformity. Usually the reported limitations are not investigated beyond a spinal x-ray. Specific soft tissue imaging techniques, such as CAT or MRI studies, are usually reserved for individuals with unremitting and severe back pain and stiffness with or without neurological findings. In contrast, most stiff and painful back complaints are initially placed in a common category and treated empirically. Although the individual may relate the complaint to some specific event such as lifting a heavy object or twisting the back excessively, it is just as common that there is no identifiable causative incident. In other words, in most cases no anatomic abnormality or other identifiable cause is found for the limitation. Patients are frequently told semi-whimsically that the major part of back complaints results from humankind's "decision" to walk erect supported in part by a vertical column of vertebrae. If the back limitation is incapacitating and resistant to the usual home remedies, the individual often seeks the help of chiropractor, an osteopath, a physical therapist or an orthopedist, clinicians much involved in relieving individuals with back complaints. In the absence of a clear causation, the limitation is managed by one or several modalities with relief ranging from non-existent to full. This is one of several examples illustrating the maxim that the more intractable a condition is to cure, the greater is the number of "cures". In other words, management of back stiffness remains far from a mature therapeutic modality.

Regardless of the cause of the back stiffness, its cause relates to some degree of muscle spasm restricting the back's range of motion, commonly asymmetrically limiting one motion more than another. Pain is a common accompaniment of this stiffness. There commonly is some associated degree of tenderness over the spastic muscle group. Traditionally, these subjects have been advised to stay in bed for several days until the complaint remits or greatly reduces. Then, several years ago, it was found that such prolonged inactivity actually caused a worsening of the disability attributed to further muscle weakness from disuse. Good muscle tone is essential to the erect posture, the full range of motion and freedom from discomfort. This observation was further supported by the quicker return to good function of individuals who resumed walking after only a couple of days of rest. While the precise mechanism of the recovery remains obscure, many investigators suspect that in addition to the resumption of normal muscular activity there may be some additional factor of recovery attributed to the effects of spinal motion.

Animal studies have suggested that one mechanism of recovery may be related to the distribution of nutrients transferring into and out of the intervertebral discs, those cartilaginous plates separating the bodies of the vertebrae. It is well established that, in arthritis of the spine, these discs narrow, causing a constriction of the small passageways between the vertebrae and creating abnormal pressure on the segmental nerves emerging through these spaces. Such pressure commonly causes muscle spasm and accompanying discomfort. If it is that pressure that gives rise to the reported pain, then improved disc-nutrition mediated by spinal motion may be the mechanism by which early return to activity (including spinal motion) following acute back discomfort results in more efficient relief of back pain.

In any event, since the discovery of the beneficial effect produced by back motion in these individuals, new therapies have been designed to enhance the early return to back motion through devices that flex and extend the lumbar vertebrae. The common name for the maneuver is "pelvic tilt," from the fact that the alternating flexion and extension of the lumbar vertebrae results in a tilting back and forth of the pelvis. In the traditional pelvic tilt exercise, the individual is supine (lying on his back) and actively rotates the pelvis forward and backward. The benefit from the pelvic tilt exercises is attributed to the strengthening of the abdominal muscles so essential in maintaining the erect posture. There may be some yet unidentified beneficial factor caused by the motion itself possibly the direct stretching of the muscles and ligaments occasioned by this range of skeletal movement. It then follows that if the active motion of pelvic tilting produces this effect, why may not passive motion through the same range of movement result in the same beneficial result.

At this point it is well to reemphasize that stiffness and discomfort are consistently associated in limited back motion. This affliction is increasingly experienced with advancing age. Past the age of 35, individuals are more susceptible to stiffness when they rise from bed in the morning or when standing after a period of immobilization from sitting. Normally, stretching or moving around brings prompt relief. The back becomes more flexible and the discomfort disappears. It has become a commonplace that the trained athlete stretches before exercise and those of us who learned the discipline of daily exercise are advised to devote a period preceding the exercise to a stretching routine.

Only recently have clinicians started to recognize that patients who complain of back pain may symptomatically benefit from passively induced flexion and extension of the lumbar spine, that is motion occasioned by an external force moving the pelvis forward and backward and, thus, flexing and extending the lumbar spine. This type of motion has been termed Continuous Passive Motion (CPM) and has been described in, among other places, "The Power of CPM: Healing Through Motion", *Continuing Care,* vol. 8, No. 10, November 1989.

A typical device applying CPM for back-pain relief is that disclosed by Riddle et al. (U.S. Pat. No. 5,500,002; issued 1996). The device of Riddle et al. provides a three-panel horizontal support on which the patient lies. The central panel supports the buttocks of the patient, and the other panels the upper body and legs, respectively. While the central panel remains static, one or both of the other panels tilt up and down. Thus, tilting the upper panel up and down, for example, will result in a motion that serves to flex the lower back region. Care must be exercised to position the body accurately so that flexion will occur in the intended segment of the spine. Beyond this consideration though is the undesirable and possibly harmful result of bending the trunk forcibly to a degree that causes pain and further spasm in the back muscles. There is no built-in mechanism to monitor the flexion according to the discomfort the device may produce. It may be postulated that the patient's position, lying instead of upright, by not utilizing the normal supporting musculature of the back may have a consequent limited beneficial effect.

Other devices have been developed that utilize the vertical position of the spine for the application of the therapeutic effect. Such a device is the one taught by Hazard et al. (U.S. Pat. No. 5,637,076; issued 1997). That device creates motion in the upright lumbar spine by means of a bladder-containing cushion placed between the subject's back and a supporting seat back. The bladder is sequentially inflated, causing a forward excursion of the lumbar spine, and then deflated, allowing the spine to return to its initial position. (The bladder-inflation/deflation cycle is carefully controlled by a pump that periodically forces air into the bladder then allows the air to escape.) This action produces CPLM of a limited yet effective degree so as to prevent the consequences, such as, stiffness and discomfort, of statically sitting in a fixed position for a prolonged period. The device has met with clinical success, particularly for drivers who must sit for long periods of time and for those office workers who are positioned before typewriters or computers for much of the day. The Hazard et al. device has been adopted by major airlines for their first-class passengers. Furthermore, a company that manufactures a chair designed to establish comfortable angles between the spine and the legs of the person seated in it now offers for sale a version of its chair that incorporates the Hazard et al. device. Thus, CPLM is slowly being recognized as a beneficial comfort mechanism to answer one of the assaults of modern civilization on the well-being of working people.

Man has for centuries, unbeknownst to him, benefited from CPM in a pre-mechanical form of transportation, horseback riding. Horses move in three gaits, walk, trot and canter. Let us examine the motion of the walk. While the horse moves forward in an uninterrupted forward progression, the back of the horse is involved in a series of repetitive thrusts as each hind leg exerts its forward motion. There is also a minimal lateral component in the motion which will be disregarded. Awareness of this intermittent acceleration is immediately apparent to the observant rider, although imperceptible to the observer on the ground. The resultant movement of the pelvis to and fro causes the lumbar spine to flex and then extend in the same manner as the active motion of the lumbar vertebrae causes the pelvis to tilt forward and backward in the pelvic tilt exercise. It is a commonplace for riders, particularly old ones, to comment that any back stiffness and discomfort they normally experience is lessened by a period of horseback riding. Pelvic tilting is the mechanism of this relief.

One of the present inventors was particularly struck by his consistent observation that riding his horse in the evening after supper resulted in the disappearance of the intense back pain and stiffness occasioned by the static upright position he necessarily maintained throughout long periods at work. A still more dramatic event occurred one morning when he awoke with extreme pain in the back and intense radiation of the pain down one leg, so-called sciatica. In some desperation, he managed to climb aboard his horse to see if the horse motion would improve his pain. To his amazement, after ten minutes of walking, he dismounted with no pain and no stiffness. Had he visited a chiropractor, instead of his horse, the relief would have been attributed to the professional manipulation. In a very real sense, he had experienced an equine adjustment.

It must be emphasized that not all horseback riding results in pelvic tilting. The tense and unsure rider's back is held rigid and resists the horse's motion, while the experienced rider maintains a relaxed and balanced position on the horse and absorbs the horse's natural motion in his back. It is not the horse but the transmitted motion of the horse that effects the beneficial effect to the rider, the CPLM.

It should be further pointed out that the experienced rider assumes a natural position of balance in which a straight line can be drawn through the point of the shoulder (the head of the humerus), the hip (the greater trochanter of the femur) and the ankle (the external malleolus of the tibia). This position translates into a straight spine, a flexion of the thigh on the trunk at a 135 degree angle and a reciprocal reverse of that 135 degrees at the knee to return the ankle to the straight line referred to above. An added benefit of this position is that it relaxes the psoas muscles, those strong muscles attached anteriorly to the lower spine and the femur which primarily flex the hips. Relaxation of these muscles further relaxes the lower spine so that it can accommodate passively to forces applied to it. Any deviation from that alignment tilts the body forward or backward resulting in increased muscle action occasioning stiffness and a loss of pelvic motion.

Therefore, what is needed is a device and method for exercise and therapy that subjects the lumbar spine to CPLM in the form of reciprocal pelvic tilts. What is also needed is such a device and method that provide this CPLM under conditions where the spine is relaxed, self-supported, and in proper vertical alignment. What is also needed is such a device and method that produce CPLM in the subject in a controlled fashion over a designated period of time in a reproducible way, with minimal instruction from a therapist or trainer. Finally, what is needed is such a device and method that after a period of self-instruction the individual can use properly without supervision.

SUMMARY OF THE INVENTION

It is the object of the present invention to provide an exercise method and device that subjects the lumbar spine of the individual to CPM through repetitive reciprocal pelvic tilts performed in a sitting position with the body balanced and postural muscles minimally contracted. This is the position that the experienced horseman has learned through centuries of instruction and experience, and it provides comfort and health. It is also the position taught by gym teachers in hygiene classes, by enlightened parents to their children and by physical therapists. In sitting and standing, this easy balanced position should be maintained as an essential discipline of healthy respect for the body. It is a further object of the present invention to provide such a method and device that can be mastered quickly by the user so that it can then be used without supervision.

As a background to understanding the device, it is well to examine the actual forces that are responsible for the pelvic tilts that are induced by a forward thrust applied to the pelvis with the individual sifting erect. The body position is characterized by inertia. It will maintain this position until some force, either external or internal, moves it. With the horse motion referenced above, the pelvis of the rider is thrust (accelerated) forward as the horse takes a step with one hind leg. The thorax does not move forward to the same degree because of its inherent inertia and the fact that the forward force on it has to be applied through its (flexible) linkage to the rider's pelvis. The remainder of the pelvic force is taken up by the motion of the lumbar vertebrae. During the relative pauses between thrusts from the alternating hind legs of the horse, the rider experiences a deceleration, causing the pelvic tilt to reverse and the lumbar spine to extend. This then is a description of the motions involved in the horse's motion and the corresponding motions of the rider. It is further pointed out that the only moving parts of the subject are the lumbar spine and the pelvis, the upper body and the legs remaining essentially immobile. Now to reproduce this action of the spine, that is, tilting the pelvis first forward and then backward, by a mechanical device, the surface on which the body rests must itself first accelerate forward, and then backward. (Unlike in the horse, these accelerations are applied to an object that has no underlying velocity.)

To see what is required to induce the repetitive back-flex motion experienced by the rider, it is useful to reflect on inertial forces which arise within an extended body of interlinked parts because of the acceleration of the body. These inertial forces account for the repetitive pelvic tilts experienced by the horseback rider.

One example of the appearance of inertial forces is provided by a tow-truck coupled to a wagon by a stretchable, compressible spring. Picture the vehicles at rest and assume that there is no friction in the wagon's wheels. At a particular time the tow truck starts moving at a constant speed V. The wagon will be put in motion only by the force exerted on it by the spring, and that spring will only exert force once it is stretched. Indeed, to a first approximation, the force exerted on the wagon will be directly proportional to the stretch in the spring. As long as the speed of the wagon is not equal to the speed of the tow truck, the spring will continue to lengthen and the force applied to the wagon will continue to increase. Thus, the acceleration of the wagon (which is the applied force divided by the mass of the wagon) will continue to increase as long as the speed of the wagon is less than that of the tow truck. Just as the wagon has a force exerted on it by the spring, so too does the spring have a force exerted on it by the wagon (an example of Newton's Third Law). The force exerted by the wagon on the spring is an example of an inertial force. Similarly, the force exerted on the tow truck by the spring which can be thought of as the inertial force of the wagon transmitted through the spring, is also an inertial force.

An inertial-force example a bit closer to the present subject matter is provided by a flexible reed, pivotably fixed at one end. If one applies a small force at the free end of the reed and perpendicular to the reed's axis, the reed will simply rotate around its pivot point. However, if the force applied to the end is great enough the reed will at first bend, as the part to which the force is applied directly accelerates faster than the rest of the reed, which is accelerated only by the intra-reed linkage that couples it to the region that is in direct contact with the force. If the force continues for a sufficiently long period (seconds in the example being discussed), the speed of the lower part of the reed will "catch up" to that in direct contact with the applied force (obviously, the alternative is the reed breaks).

In the case of the horse at a walk, the saddle alternately undergoes positive and is negative acceleration about the average walking speed of the horse. (Negative acceleration is commonly called "deceleration." During the positive acceleration, the forward speed of the horse increases to a value above the average forward speed; during negative acceleration (deceleration) it falls back below the average speed.) It is the acceleration, rather than the forward speed per se that causes the tilting of the pelvis. The tilting of the pelvis is analogous to the reed example above. The rider's buttocks and legs, being in direct contact with the horse, accelerate forward and then decelerate. As they accelerate forward, the upper body is initially left behind, as it were. For a few seconds the lower body moves forward with respect to the upper body. Since, with proper riding form, the upper body remains upright during this interval, there must be a displacement between the upper and lower body. This occurs by virtue of the pelvic bone, which bridges the gap, tilting, so that both the angle that it makes with the lower back and the angle that it makes with the thighs change. Once this change has reached a maximum, the upper body follows along. At that point or shortly thereafter, the saddle undergoes deceleration. Since the buttocks and legs are in direct contact with the saddle, this part of the rider's body follows this deceleration closely. Once again, however, the upper body behaves differently. Since it is not in direct contact with the horse, it continues moving forward at a constant speed until acted upon through its link with the lower body, i.e., through the lower back and pelvic bone. As a result, the pelvic tilt now goes in the other direction.

The present device essentially is a mechanism that provides a seat that alternately accelerates forward and backward at a frequency that roughly approximates that of a horse at a walk. These repetitive cycles occur sixty times a minute. The seat must be readily mountable. It must not only support the weight of the body in the sitting position but be so constructed that the seat itself does not slip forward or backward in response to the movement. Such a displacement of the seat would vitiate the power of the thrust rather than transmit it to the pelvis.

The final form of a device meeting the stated requirements evolved into a platform supporting a pedestal on top of which was mounted a seat resembling a Western-style saddle with a high front prominence (the saddle pommel) and a high back prominence (the saddle cantle), as well as sufficient padding to provide comfort. The propulsive force comes from an electric motor mounted under the platform. It was found that the high torque force required to alter the direction of the motion could only be obtained by a direct current motor rather than the more common indirect current motor. To convert the electric current for this purpose in turn necessitated a transformer. Also incorporated in the power mechanism was a rheostat to control the rate of the cycles. The position of this rheostat must be easily accessible to the operator or the supervising person. There must also be sufficient superstructure to provide a fixed support for the individual during the mounting or dismounting from the apparatus, and in the case the individual loses his or her balance while exercising.

Thus, the present invention is based on a device which allows the subject to sit in the manner described on a support that comes into contact with his or her legs and buttocks, a support that, once the subject has assumed the proper position, can provide back and forth translational motion in a horizontal direction. It can be seen from the above discussion of inertial forces that some experimentation is invited with respect to the nature of the horizontal motion with respect to the acceleration presented as a function of time. This will be in part a function of the total distance of horizontal movement (the "excursion") and the period of each cycle, that is, the time required for the device to go through a complete cycle and return to the starting point again. However, in addition, it is possible to also vary the shape of the acceleration curve that is applied. For example, one may move the support back and forth in accordance with a sinusoidal function: $x=A\cos\omega t$, where t is time, A is the maximum excursion, and $\omega=2\Pi/T$ where T is the period of each cycle. This will result in an acceleration curve of $a=-(2\Pi\omega)^2A\cos\omega t$, that is, of $a=-(2\Pi\omega)^2x$. Alternatively, one may make the support move at a constant speed through most of the excursion, with acceleration occurring only at the two extremes as the support stops moving in one direction at a particular speed and shifts to moving in the other direction at the same speed.

Although it is not necessary to actually have a simulated saddle on the device of the present invention, the saddle shape is something that encourages the proper posture in the person being treated. For conciseness, therefore, the continuing description of the device and method will refer to the patient support as a saddle. Also, although not essential to the device of the present invention, most embodiments of it will incorporate some kind of platform surrounded by a railing; therefore, for definitiveness, it will be assumed in the description below that the device is so equipped.

Let us now go through a typical exercise of the individual's use of the device. First, he steps up on the platform and sits down in the saddle. The supervisor may have to make an adjustment in the height of the saddle if the initial estimate of this position was inaccurate. The individual should sit erect with the shoulders, the hip bone and the ankle bone in substantially the same plane. His hips should assume an angle of 135 degrees with the trunk and the knees a reciprocal 135 degrees bringing them back on line with the shoulders and hips. The feet should comfortably rest on the platform, preferably with the soles flat on the surface. After he feels confidently aligned, he, or the supervisor, turns the rheostat knob to a speed that moves the individual's pelvis forward and backward in continuous even cycles. The movement should not increase any pain the individual may be experiencing. Gradually, if not initially, the individual should experience some motion in the lumbar spine and get a sense of being relaxed rather then stiff in the upper body. The optimal rate of the cycles appears to be about sixty per minute. This optimal rate should be reached by gradually twisting the control knob. If the individual's back has noticeable stiffness and soreness, he should in a period of minutes begin to notice some increase in the flexibility of the lower back. The natural tendency will be to stiffen the back in a protective reflexive action. But in time, and at an accommodating rate of the device, he should note some benefit in the form of increased flexion and extension of the lumbar vertebrae and accompanying tilting of the pelvis.

In review, the essentials of the exercise consist of the proper leveling of the seat, the easy mounting of the device, the assumption of a relaxed and balanced sitting position, the initiating of the to and fro motion of the machine, adjustment of the optimal rate of the cycles, the experience of the lumbar spine moving in synchrony with the moving platform, performance of the exercise for approximately ten minutes, stopping the motion and dismounting from the device, and realizing increased flexibility of the spine and relief of any accompanying discomfort in the back.

The use of definitive language in the above account was intended to more readily convey the nature of the method and device of the present invention, and not to limit in anyway the scope of the present invention. Rather, the discussion above with specific terms is considered to be merely illustrative of the scope of the present invention and it is to be further understood that numerous changes may be made by those knowledgeable in the field without straying beyond that scope.

DETAILED DESCRIPTION OF THE PREFERRED EMBODIMENT

There are a number of basically equivalent ways of practicing the method of the present invention. In what follows the method will be discussed in terms of the Preferred Embodiment device of the present invention, which is illustrated in the Figures. The method of the Preferred Embodiment is determined in part by the device and will be described along with the device.

Figure 1:
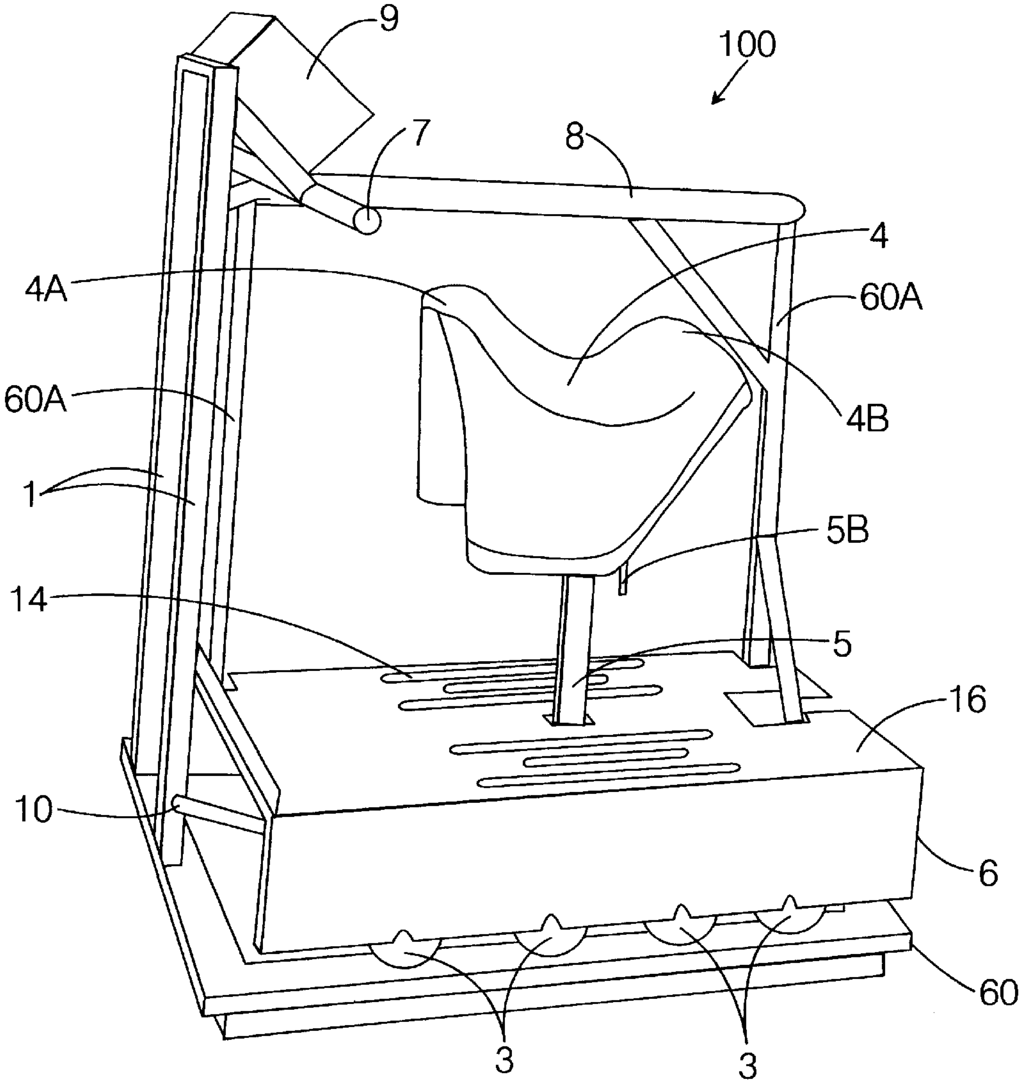
FIG. 1 is a perspective view from the left side of the Preferred Embodiment device of the present invention.
Figure 2:
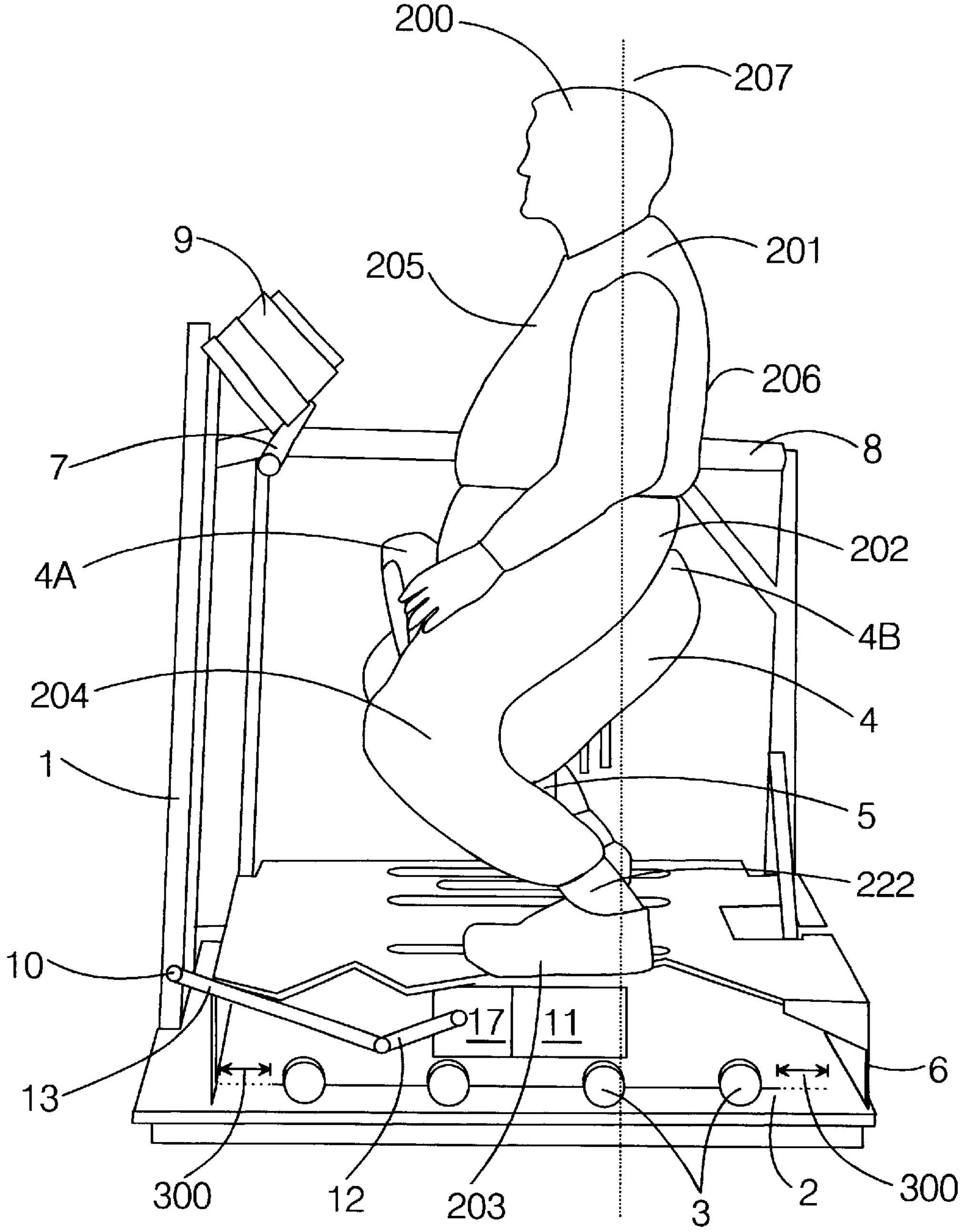
FIG. 2 shows a back-exercise patient properly mounted on the Preferred Embodiment device of the present invention. A part of the device is cut away in this depiction, so as to show some of the components that are normally shielded, components including the linkage used to activate the device.

The overall appearance of the Preferred Embodiment device 100 of the present invention is shown in the perspective views of FIG. 1 and FIG. 2. The latter shows a person 200 properly mounted in a saddle-seat 4 of the device. Note the stance of the person 200 and in particular how his shoulders 201, hips 202, and ankles 222 all lie substantially in the same plane 207. Note further, with reference to FIG. 2, the shape of the saddle-seat 4, which has a front prominence 4A, also called a pommel, and a back prominence 4B, also called a saddle cantle. The shape of the saddle 4 is intended to induce the thighs 204 to form an angle of approximately 135 degrees with the upper part of the body 205. This is considered to give the proper vertical orientation to the back 206 and to place the back 206 in a self-supporting configuration. The horizontal arrows 300 in FIG. 2 suggest the translational motion that the moving frame 6 undergoes when the device 100 is in operation.

With continuing reference to FIG. 1, it can be seen that the saddle-seat 4 is affixed to a seat-support pedestal 5, which in turn is attached to and rises from the moving frame 6, passing through a platform 16 that, in the Preferred Embodiment device 100 is made of wood. Further, anti-slip strips 14 are affixed to the platform 16 to assist the person 200 in mounting and dismounting the device 100.

Figure 3:
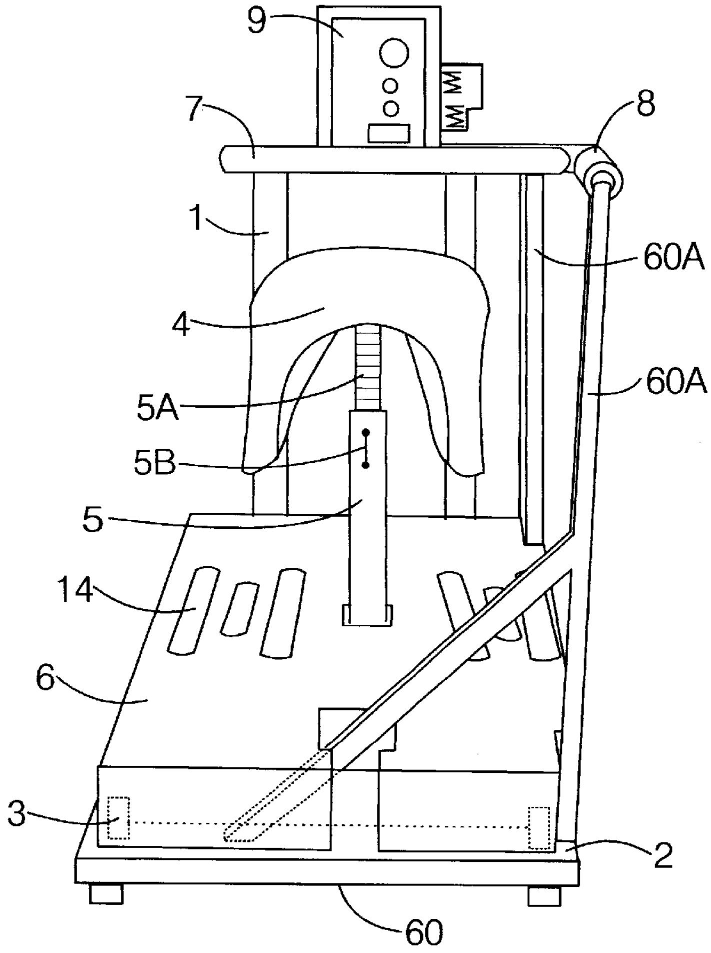
FIG. 3 shows a back view of the Preferred Embodiment device of the present invention.
Figure 4:
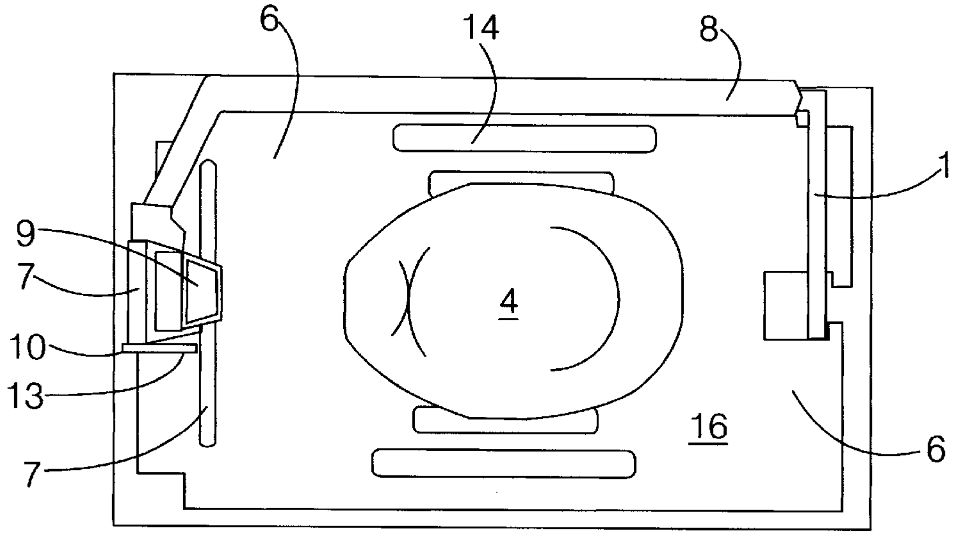
FIG. 4 is a top-down view of the Preferred Embodiment of the device of the present invention.

Among other functions, the platform 16, which is affixed to and moves with the moving frame 6, serves to shield a number of the moving parts of the apparatus from the person 200, while also providing him a surface on which to stand while mounting and dismounting the saddle-seat 4. The seat-support pedestal 5 is adjustable in height so as to allow the person 200 to have his height at the level most conducive to the desired result from the device 100. Many height-adjustment mechanisms for adjusting the height of a seat are known and any mechanism that is suitable for providing simple and easy adjustment of the seat height may be used in the device according to the invention. In the Preferred Embodiment, a simple ratchet mechanism 5A with an actuating lever 5B is used, as can be seen in FIGS. 1 and 3. It appears that the best height is one that ensures that the feet 203 of the person 200 are flat on the platform 16, as shown in FIG. 2. An alternate acceptable configuration has the feet 203 flexed so just the toes are touching the platform 16.

The moving frame 6 moves on and with respect to a fixed frame 60, their point of contact being wheels 3, which are affixed to the moving frame 6 and rest rollingly on the fixed frame 60. In the Preferred Embodiment, the basic structures of both the moving frame 6 and the fixed frame 60 are made of steel, though certain non-steel components are attached to them. The fixed frame 60 provides general structural integrity for the device 100 as a whole as well as a framework within which and on which the moving frame 6, when activated, moves back and forth (translates), as depicted by arrows 300 in FIG. 2. When the moving frame 6 is forced to move, the wheels 3 roll along a base 2 of the fixed frame 60, thereby allowing the moving frame 6 to smoothly translate back and forth within the confines of the fixed frame 60. In the Preferred Embodiment device of the present invention, four wheels 3 are arranged on each side of the moving frame 6, as can be seen in FIG. 1. In the Preferred Embodiment method of the present invention, the moving frame 6, when the device is activated, is caused to translate two inches in each direction for a total movement of four inches from the rear-most position to the front-most position of the moving frame 60 and, consequently, of the person 200. As will be seen with reference to FIG. 5, the excursion magnitude in the Preferred Embodiment device is established by the choice of linkage used between the motive force and the fixed frame 60 and could be changed easily should reason arise to do so. The four-inch excursion of the Preferred Embodiment method was found by the inventors to lead to the best therapeutic practice.

Figure 5:
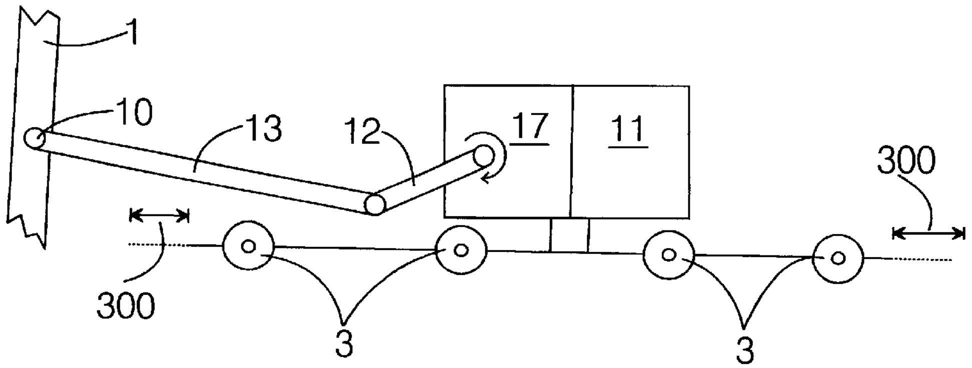
FIG. 5 shows some detail of the mechanism used to drive the saddle mount of the device that is the Preferred Embodiment of the present invention.

The particular mechanism used in the Preferred Embodiment device 100 for translating the moving frame 6 back and forth is illustrated schematically in FIG. 5. The motive force is provided by a DC motor 11 coupled to a gear box 17. In the Preferred Embodiment, the motor 11 is a Dayton DC Motor Model 2M168D, and the gear box 17 is a Dayton Speed Reducer Model 920. As can be seen from further reference to FIG. 5, affixed to the output of the gear box 17 is an axle extension arm 12 which in turn is coupled to a swing arm 13. The conversion of the rotary motion provided by the motor 11 working through gear box 17 to the desired translational motion of the moving frame 6 is achieved by pivotably connecting the swing arm 13 to the fixed frame 60 via a swing-arm pivot 10, located on a vertical member 1 of the fixed frame 60. In particular, this linkage and motive source translate the moving frame 6 back and forth with respect to the fixed frame 60. It can be seen that the translational excursion in each direction (forward and back) will be equal to the effective length of the extension arm 12, as the moving frame 6 moves back and forth on the wheels 3, some of which are shown in FIG. 5. In the Preferred Embodiment, the extension arm 12 is two inches in effective length (which is the distance between the point at which the extension arm 12 attaches to the swing arm 13 and the point where it attaches to the output of the gear box 17.).

The speed of the motor 11 and, hence, the rate at which the extension arm 12 causes the moving frame 6 to translate back and forth with respect to the fixed frame 60 is set with the controls 9, as are shown schematically in FIG. 1, FIG. 2, FIG. 3, and FIG. 4. In the Preferred Embodiment the controls 9 consist of a Dayton DC Speed Control, and a means for converting 110-volt ac voltage to variable-level dc voltage. The person 200 can vary the dc voltage to the motor 11 while seated on the saddle-seat 4. In the alternative, the professional worker overseeing the exercise or therapy can vary that level, and hence the speed of the motor 11 and, thus, the speed with which the moving frame 6 translates back and forth.

It can be seen by the nature of the linkage coupling the gear box 17 to the fixed frame 60 that the motion of the moving frame 16 (and, hence, the lower body of the person 200) follows a sinusoidal curve. Among other things, this means that the translation speed will be a maximum and the acceleration a minimum as the saddle-seat 4 is passing through its neutral position. Conversely, the acceleration will be a maximum and the speed a minimum when the saddle-seat 4 is at the maximum-excursion points on its translational trajectory. It is at these two extremes, therefore, that the inertial force applied by the upper body to the lower back will be at a maximum.

In the Preferred Embodiment method of the present invention, a person 200 desiring exercise or therapy for his back first steps onto the platform 16, grabbing a padded hand rail 8 for stability as he mounts the saddle-seat 4. Alternatively, he might use the handlebars 7 as an aid to mounting the saddle-seat 4. By trial and error, either the person 200 or the person overseeing his activity will have adjusted the pedestal 5 so that when the person 200 is seated on the saddle-seat 4 as described above, his or her feet 203 will be flat on the platform 16.

With the controls 9, motor 11, gear box 17, and linkage of the Preferred Embodiment, it is possible to set the translational frequency of the saddle-seat 4 anywhere ranging from essentially zero (say, 1 cycle per minute) up to 80 cycles per minute. (Here, "frequency" refers to the number of complete translational cycles that are completed in unit time, here stated in cycles per minute.) The preferred therapeutic range is from 40 to 60 cycles per minute. If one chooses a frequency that is too low, the upper body and lower body may move as a unit, with no pelvic tilt action; in other words the device is not efficacious in establishing CPM pelvic tilts if the frequency is set too low. Too high a frequency may result in other deleterious effects.

At the outset of a session, when the back of the person 200 will be relatively stiff, the frequency should be relatively low, so that the force exerted on the spine and back muscles is minimal. As the person 200 becomes acclimated to the motion and the stiffness begins to relax, the frequency can be increased, normally to 60 per minute. This rate seems to produce the optimum pelvic tilts once the person 200 is relaxed, leading to optimum stretching of the lumbar muscles with the consequent production of relaxation and relief of discomfort. The most desirable length of a particular session will vary with the individual, though ten minutes of sustained passive motion usually appears to be optimal.

Regardless of the particular embodiment of the invention, the key is to induce in the person 200 the type of pelvic motion that riding a horse at the walk induces in an experienced equestrian. Therefore, the therapeutic effectiveness of the device 100 depends on the ability of the person 200 to relax sufficiently to allow the fluid motion of the lumbar spine that an experienced equestrian naturally experiences. This in turn means that the person 200 should remain relaxed, balanced, and in proper vertical alignment as the lumbar spine follows and absorbs the pelvic thrusts. The object is to decouple the upper back from the lower back to the extent that the motion of the moving frame 60 moves the lower body forward and back while the inertia of the upper body keeps the upper body relatively fixed. This is the mechanism by which the CPM flexes and extends the spine, resulting in the pelvic tilts. There should be relatively little motion of the upper body as its inertia maintains its upright position, thereby naturally transmitting the pelvic thrusts into fluid, wavelike motion of the lumbar vertebrae, which then undergo flexion smoothly followed by extension. It is found that some individuals are able to easily adopt the stance and "decoupling" needed for this motion to take place, while others have to have considerable advice from the therapist or trainer (just as some beginning horseback riders need more advice than others) before they can obtain the intended benefits.

The description of the details of the Preferred Embodiment of the method and device of the present invention is not intended to limit in any way the scope of the present as described in the SUMMARY and elsewhere. Persons skilled in equestrian arts and in the healing arts, in particular those related to relieving back pain and stiffness, will be able to devise many different approaches that fall within the general description of the present invention.

We claim:

1. A continuous passive lumbar motion (CPLM) therapy device for exercising a lumbar spine region that is between an upper torso and a lower torso of a subject, said device comprising:

a platform including a fixed frame having a first end and a second end and a sliding platform slidably mounted on said fixed frame;

a height-adjustable support seat mounted on said sliding platform, said support seat having a front support and a back support, each of which rises substantially vertically from said support seat, wherein said support seat with said front support and said back support provides a secure seating for said lower torso and restrains said lower torso from moving forward or rearward relative to said support seat while exercising;

a translational-motion drive that drives said sliding platform in a horizontal, cyclical motion in a forward direction toward said first end of said fixed frame and a rearward direction toward said second end, wherein a rearward travel of said sliding platform toward said second end is co-planar and 180° different from a forward travel of said sliding platform in toward said first end; and a control means mounted on said platform, said control means providing adjustability of an operating frequency of said cyclical motion within a frequency range that allows said upper torso of said subject to move relative to said lower torso at said lumbar spine region.

2. The device described in claim 1, wherein said support seat is supported on said sliding platform by a height-adjustable column having a lower end that is attached to said sliding platform and an upper end that is attached to said support seat.

3. The device described in claim 1, wherein said platform further includes a linkage that couples said fixed frame to said sliding platform, and wherein said translational-motion drive means includes a high-torque dc motor that, when in operation, moves said sliding platform via said linkage in a horizontal translational back-and-forth motion relative to said fixed frame.

4. The device described in claim 3, wherein said adjustable control means includes a a variable speed control means for said dc motor, wherein said variable speed control means produces a variable dc voltage that is applied to said dc motor.

5. The device described in claim 4, wherein said variable speed control means provides a variable operating frequency from zero cycles per minute up to an upper frequency of eighty cycles per minute, and wherein said sliding platform oscillates in said horizontal translational back-and-forth motion at an operating frequency selected on said variable speed control means.

6. The device described in claim 5, wherein said operating frequency is 60 cycles per minute.

7. The device described in claim 3, wherein said linkage provides a horizontal translational motion of a certain excursion.

8. The device described in claim 7, wherein said excursion is approximately four inches.

9. The device described in claim 1, wherein said fixed frame includes parallel tracks and said sliding platform has a platform underside with a plurality of rollers, and wherein said rollers slide in said parallel tracks on said fixed frame.

10. The device described in claim 1, wherein said front support is a front prominence resembling a saddle pommel and said back support is a back prominence resembling a saddle cantle.

11. The device described in claim 1, wherein said fixed frame includes a superstructure that has vertical supports and a hand support mounted on said vertical supports at a height that is readily accessible by said human subject seated on said support seat.

12. The device described in claim 11, wherein said hand support includes a pair of handlebars mounted on said vertical supports.

13. The device described in claim 12, wherein said hand support includes a horizontal hand rail mounted on said vertical supports.

* * * * *